US00PP35452P2

(12) United States Plant Patent
Meilland

(10) Patent No.: US PP35,452 P2
(45) Date of Patent: Nov. 7, 2023

(54) MINIATURE ROSE PLANT NAMED 'MEILPIQUET'

(50) Latin Name: *Rosa hybrida*
Varietal Denomination: MEILPIQUET

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/086,922

(22) Filed: Dec. 22, 2022

(51) Int. Cl.
*A01H 5/02* (2018.01)
*A01H 6/74* (2018.01)

(52) U.S. Cl.
USPC ..... Plt./118

(58) Field of Classification Search
USPC ..... Plt./118, 125
CPC ... A01H 5/02; A01H 5/00; A01H 6/74; A01H 6/749
See application file for complete search history.

(56) References Cited

U.S. PATENT DOCUMENTS

PP9,652 P 10/1996 Meilland
PP14,274 P2 * 11/2003 Meilland ..... A01H 5/02 Plt./118
PP16,202 P2 1/2006 Radler

OTHER PUBLICATIONS

Mobilian, Star Roses and Plants to showcase new varieties at Cultivate'22, Nursery Management 2022, retrieved on Mar. 9, 2023 at https://www.nurserymag.com/news/star-roses-and-plants-to-showcase-new-varieties-at-cultivate-22/, 14 pp. (Year: 2021).*
Star Roses and Plants Sunblaze Lemon, retrieved on Mar. 9, 2023 at https://www.starrosesandplants.com/plants/sunblaze-lemon/, 4 pp. (Year: 2023).*

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'MEILPIQUET', is disclosed. The new variety forms attractive, double cream, colored flowers. Attractive glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida. 'MEILPIQUET'.*
Variety denomination: 'MEILPIQUET'.

STATEMENT REGARDING PRIOR DISCLOSURES BY THE INVENTOR

The first offer for sale of the new variety was Mar. 4, 2022 in the United States of America. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was an unnamed seedling (not patented). The male parent (i.e., the pollen parent) of the new variety was an unnamed seedling (not patented) from the cross between a different unnamed seedling (not patented) and the 'RADTKO' variety (U.S. Plant Pat. No. 16,202).

The parentage of the new variety can be summarized as follows:

Unnamed Seedling x (Different Unnamed Seedling x 'RADTKO')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms cream colored flowers, (b) produces double flowers, and (c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the unnamed seed parent displays flowers that are true intense yellow in color, whereas the new variety displays cream colored flowers. In addition, the unnamed pollen parent (Different Unnamed Seedling x 'RADTKO') produces lower color surface when in full bloom compared to the new variety. Moreover, the new variety can be readily distinguished from other similar non-parental varieties. For example, the 'MEIFERJAC' variety (U.S. Plant Pat. No. 9,652) produces smaller sized flowers that are orange in color compared to the new variety which produces cream colored flowers. As another example, the 'Meiskaille' variety (U.S. Plant Pat. No. 14,274) exhibits petal color near Yellow Group 13A and produce 96 on average pistil number, whereas the new variety exhibits petal color near Yellow Group 8D when open and produces 49 on average pistil number.

The new variety has been named 'MEILPIQUET'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately one year of age and were observed during May while budded on their own roots and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a flowering stem.

Element 11—illustrates a specimen of a floral receptacle showing arrangement of the stamens and pistils.

Element 12—illustrates a specimen of a floral receptacle showing arrangement of the pistils (stamens removed).

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of one-year-old specimens of the new variety during May while budded on their own roots and growing outdoors at Le Cannet des Maures, Var, France.

Botanical classification: *Rosa hybrida* cultivar MEILPIQUET.

Commercial classification: Miniature Rose Plant.

Plant:

*Habit*.—Bushy.

*Height*.—Commonly between 25 cm to 35 cm.

*Width*.—Commonly between 35 cm to 45 cm.

Branches:

*Color*.—Young stems: commonly near Yellow-Green Group 144A. — adult wood: commonly near Yellow-Green Group 144A amply covered with near Green Group 143A.

*Length*.—From the crown to the flower is typically between 15 cm to 20 cm.

*Diameter*.—Typically between 0.3 cm to 0.4 cm.

*Young shoots*.—Anthocyanin coloration: absent.

*Thorns*.—Configuration on adult stems: slightly concave and elongated on the upper surface and very concave on the under surface. — long prickles — quantity: approximately 13 thorns on average per 10 cm long young stem and approximately 15 thorns on average per 10 cm long adult stem. — long prickles — length: typically between 0.6 cm to 0.8 cm on young stems and typically between 0.5 cm to 5 0.8 cm on adult stems. — long prickles — width: approximately 0.2 cm on average on young stems and approximately 0.4 cm on average on adult stems. — long prickles — base: shape is narrow obovate and 10 short on young stems; shape is majority amply obovate and sometimes narrow obovate on adult stems. — long prickles — color on young stems: commonly near Yellow-Green Group 144B. — long prickles — color on adult stems: commonly near Greyed-Orange Group 164A slightly shaded at the base with near Greyed-Red Group 179B and covered with near Yellow-Green Group 144A to the tip. — small prickles — quantity: absent.

*Internode*.—Numbers on the entire branch: typically between 3 to 5. — length: typically between 2.0 cm to 3.0 cm.

Foliage:

*General appearance*.—Rather dense, darker with a glossy aspect.

*Number of leaflets*.—3, 5, 7; most often 7.

7 *leaflets leaf*.—Length: approximately 8.0 cm on average. — width: typically between 5.0 cm and 8.0 cm.

*Terminal leaflet*.—Length: typically between 3.0 cm to 3.5 cm. — width: typically between 2.0 cm to 2.5 cm.

*New foliage*.—Upper surface color: commonly near Green Group 139A. — under surface color: commonly near Green Group 137B. — anthocyanin coloration: absent.

*Adult foliage*.—Upper surface color: commonly near Green Group 139A. — under surface color: commonly near Green Group 137B. — anthocyanin coloration: absent.

Leaflets:

*Shape*.—Top: acuminate. — base: obtuse.

*Glossiness of upper surface*.—Strong.

*Texture*.—Upper and under surfaces are thick.

*Smoothness*.—Upper surface is smooth; under surface is bumpy.

*General appearance*.—Oval.

*Serration*.—Small and single.

*Undulation on the margin*.—Weak.

*Venation*.—Color is commonly near Yellow-Green Group 144B and pattern is imparipinnate.

*Petiole rachis*.—Color of upper surface: commonly near Yellow-Green Group 144B edged with near Green Group 139A. — color of under surface: commonly near Yellow-Green Group 144A. — texture: upper surface is few glandular, under surface is very few prickles. — rachis of terminal leaflet: length is approximately 3.5 cm on average and diameter is approximately 0.1 cm on average.

*Petioles*.—Upper surface: no glandular. — under surface: no prickles. — color of upper surface: commonly near Yellow-Green Group 144B edged with near Green Group 139A. — color of under surface: commonly near Yellow-Green Group 144A. — length: approximately 1.5 cm on average. — diameter: approximately 0.1 cm on average.

*Stipules*.—Length: typically between 0.9 cm to 1.2 cm. — width: approximately 0.35 cm on average. — general appearance: rather broad. — texture: smooth. — color of upper surface: commonly near Yellow-Green Group 144A. — color of under surface: commonly near Yellow-Green Group 144A.

Inflorescence:

*Number of flowers per stem*.—Between 2 and 5 flowers per stem.

*Lastingness of the bloom*.—On the plant: approximately 7 days. — in vase: not tested.

*Bud*.—Shape: conical. — size: small. — length: approximately 2.3 cm on average. — width: approximately 1.5 cm on average. — color as calyx breaks: upper surface: internal petals are commonly near Yellow Group 9A and external petals are commonly near Yellow Group 7A at the proximal end evolving to Yellow Group 11D at the distal end, no basal spot. under surface: inner petals are commonly near Yellow Group 7A and external petals are commonly near Yellow Group 7B at the proximal end evolving to Yellow Group 11D at the distal end, no basal spot.

*Sepals*.—Number: commonly 5. — length: approximately 1.8 cm on average. — width: approximately 0.6 cm on average (on median part). — shape: at the top: slightly elongated and narrow. at the base: flat at union with the receptacle. — extensions: medium on 3 sepals. — upper surface: texture: tomentous. color: commonly near Yellow-Green Group 144A covered with near Green Group 143B and with near Green-White Group 157B on hairs. — under surface: texture: smooth. color: commonly near Green Group 143C covered with near Green Group 143B.

*Receptacle*.—Color: commonly near Green Group 143C shaded with near Green Group 143B. — length: approximately 1.0 cm on average. — width: approximately 0.6 cm on average (on median part). — surface: smooth. — shape: funnel shaped.

*Peduncle*.—Length: approximately 1.6 cm on average. — width: approximately 0.2 cm on average. — surface: glandular. — color: commonly near Green Group 143C.

*Flower*.—Diameter when open: typically between 6.0 cm to 6.5 cm. — depth of the flower: approximately 2.5 cm on average. — shape: flat cup shaped. — shape when viewed from above: rounded. — shape of the upper part of the flower profile: flattened convex. — shape of the lower part of the flower profile: flattened convex. — type: double. — number of petals under normal conditions: typically between 30 to 45 petals. — petals: shape: obovate (acute at the base and rounded at the top). texture: soft. length: approximately 3.0 cm on average. width: typically between 1.4 cm to 2.0 cm. — undulation of the petal: very weak. — reflexing of the petal: very weak. — petal incision: very weak. — petal arrangement: imbricated without petaloids. — petal drop: petals drop off cleanly before drying. — fragrance: none. — discoloration of the flower: yes, almost white. — color when opening: basal spot on the upper surface: absent. upper surface: internal petals are commonly near Yellow Group 7B at the proximal end evolving to near Yellow Group 8C at the distal end; external petals are commonly near Yellow Group 7B at the proximal end evolving to near Yellow Group 8D at the distal end. basal spot on the under surface: absent. under surface: internal petals are commonly near Yellow Group 7C at the proximal end evolving to near Yellow Group 8C at the distal end; external petals are commonly near Yellow Group 7C at the proximal end evolving to near Yellow Group 8D at the distal end. — color of the open flower: basal spot on the upper surface: commonly near Yellow Group 8A. upper surface of the flower: commonly near Yellow Group 8D. basal spot on the under surface: commonly near Yellow Group 8A. under surface of the flower: commonly near Yellow Group 8D. — color of the flower when fading: same color as the open flower. — anthers: number is typically between 45 to 55, length is approximately 0.2 cm on average, width is approximately 0.1 cm on average, coloration is commonly near Yellow-Orange Group 22A, and arrangement is regular around styles. — filaments: length is approximately 0.3 cm on average and coloration is commonly near Yellow-Green Group 150C. — styles: length is approximately 0.5 cm on average, coloration is commonly near Red-Purple Group 57A on the apical part and near White Group 155C on the basal part, and number is approximately 49 on average. — stigmas: length is approximately 0.1 cm on average and coloration is commonly near Yellow Group 3A. — pollen: color is commonly near Yellow Group 13A and amount is abundant. — hips: not available at this stage; new variety does produce hips.

Development:

*Vegetation*.—Medium.

*Blooming*.—Early in the season, abundant and recurrent, typically from May to October in France.

*USDA hardiness zone*.—Zone 5 to 11.

*Tolerance to disease*.—Good, and particularly against rust (*Phragmidium* sp).

The new 'MEILPIQUET' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEILPIQUET' characterized by the following combination of characteristics:

(a) forms cream colored flowers, (b) produces double flowers, and (c) exhibits a bushy growth habit;

substantially as herein shown and described.

* * * * *

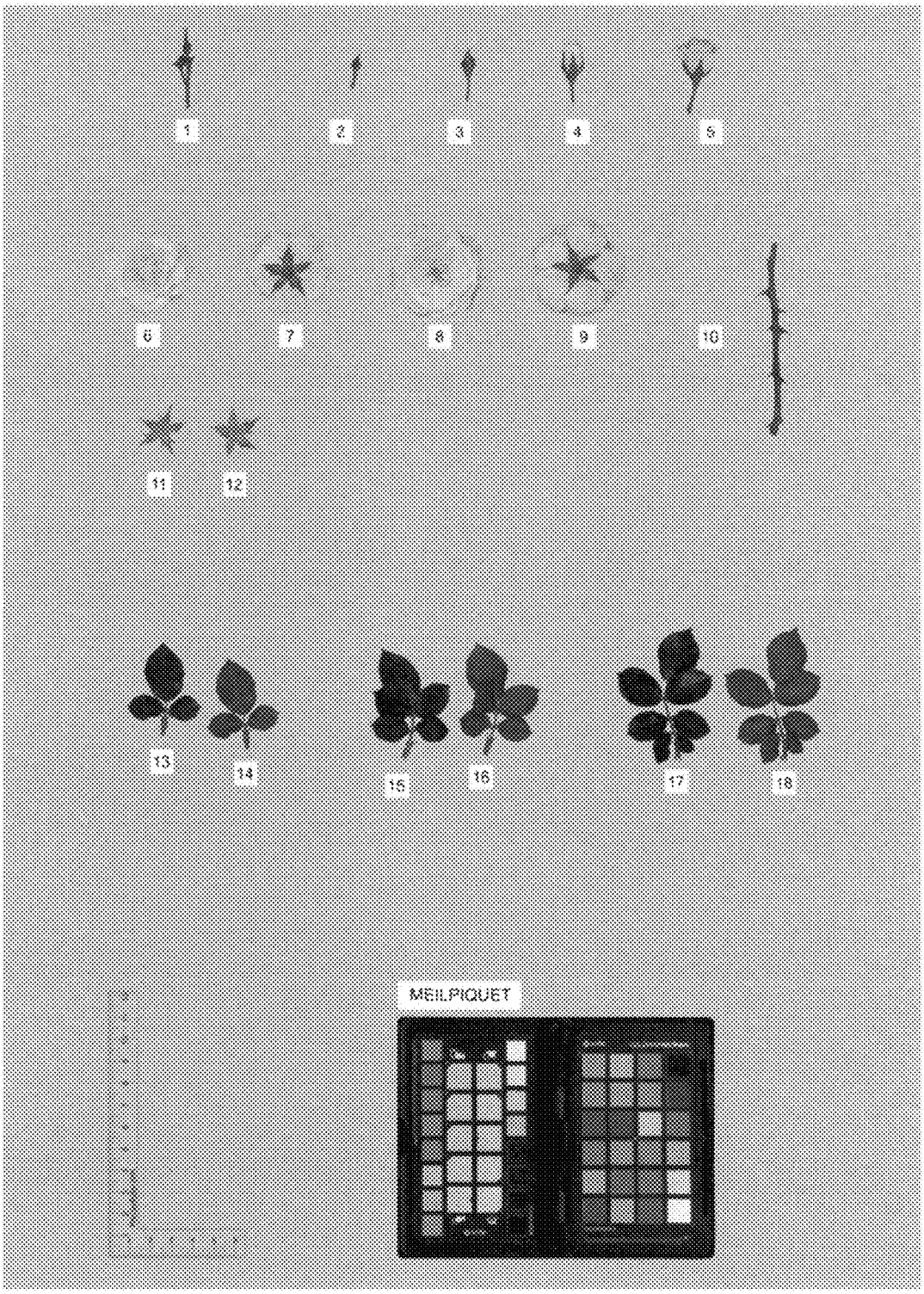
1
2
3
4
5
6
7
8
9
10
11
12
13
14
15
16
17
18
MEILPIQUET